United States Patent [19]

Moran, Jr.

[11] Patent Number: 4,945,183

[45] Date of Patent: Jul. 31, 1990

[54] PROCESS FOR THE PREPARATION OF 4-PHENYLQUINOL

[75] Inventor: Edward F. Moran, Jr., Wenonah, N.J.

[73] Assignee: E. I. Du Pont de Nemours and Company, Wilmington, Del.

[21] Appl. No.: 443,376

[22] Filed: Nov. 30, 1989

[51] Int. Cl.$^5$ ............................................. C07C 45/28
[52] U.S. Cl. ..................................... 568/309; 568/763
[58] Field of Search ................................ 568/309, 763

[56] References Cited

U.S. PATENT DOCUMENTS

| | | | |
|---|---|---|---|
| 2,704,772 | 3/1955 | Young | 568/807 |
| 3,873,580 | 3/1975 | Rennie | 568/309 |
| 4,560,804 | 12/1985 | Yeh et al. | 568/309 |
| 4,639,298 | 1/1987 | Kreh et al. | 568/309 |
| 4,647,349 | 3/1987 | Kreh et al. | 568/309 |
| 4,670,108 | 6/1987 | Kreh et al. | 568/309 |

*Primary Examiner*—James H. Reamer

[57] ABSTRACT

Preparation of 4-phenylquinol by oxidation of biphenyl using an aqueous mixture of cerium methanesulfonic acid in which the ratio of cerous to ceric methanesulfonic acid is in the rate of 0.2 to 50 mole percent.

6 Claims, 1 Drawing Sheet

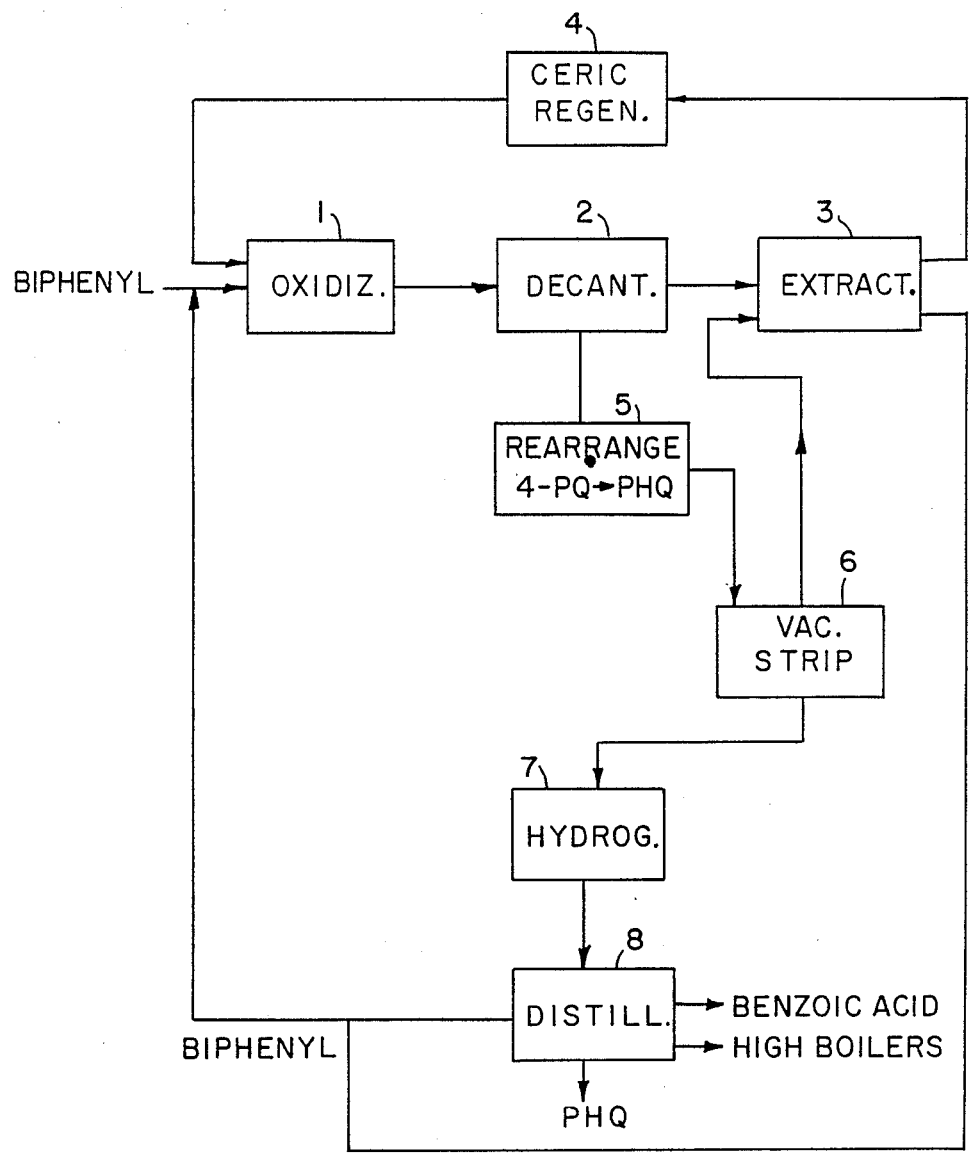

PROCESS FOR THE PREPARATION OF 4-PHENYLQUINOL

FIELD OF THE INVENTION

This invention relates to the preparation of 4-phenylquinol, (hereinafter sometimes referred to as "4-PQ") i.e.

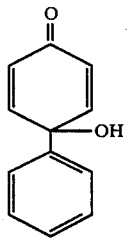

by the oxidization of biphenyl, i.e.

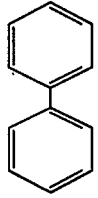

using as oxidizing agent an aqueous mixture containing ceric methylsulfonate. The 4-phenylquinol may be readily isomerized to phenylhydroquinone, (sometimes hereinafter referred to as PHQ), a compound known to be a useful monomer in the preparation of plastic materials.

BACKGROUND OF THE INVENTION 4-phenylquinol is a known compound, and a process for its preparation (modified Bamberger's reaction) and isomerization to phenylhydroquinone are disclosed in Chemical Abstracts 1943 2181i.

The use of ceric methylsulfonate as an oxidizing agent for organic compounds dissolved in an aqueous-organic cosolvent system is known and taught in U.S. Pat. No. 4,670,108 to Kreh et al. In this patent the ceric ion is regenerated electrolytically, and the reaction is termed to be an "indirect electrochemical oxidation". The term refers to an oxidation of a compound which proceeds in two steps such that the first step provides a metal ion oxidant (ceric ion) by anodic charge exchange and the second step comprises reacting the metal ion oxidant with a aromatic compound to produce carbonyl containing compound. The indirect electrochemical oxidation of the organic substrate can be conducted in the electrochemical reactor (in-cell) or in a separate reactor (ex-cell).

The oxidation of biphenyl using a solution containing ceric ammonium nitrate to produce 2-phenylbenzoquinone, i.e.

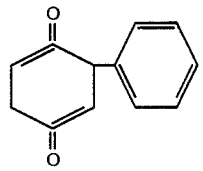

is disclosed in U.S. Pat. No. 3,873,580 to Rennie. 2-phenylbenzoquinone can be reduced with hydrogen to produce phenylhydroquinone, i.e.

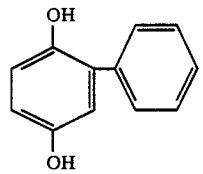

SUMMARY OF THE INVENTION

The present invention is a process for the preparation of 4-phenylquinol which comprises oxidizing at a temperature in the range of 20° to 90° C., biphenyl dissolved in an organic solvent, with an aqueous mixture containing cerous methylsulfonate, ceric methylsulfonate and methanesulfonic acid, in which the mole ratio of cerous methylsulfonate to ceric methylsulfonate is in the range of 0.2 to 50 mole percent, and the organic solvent is substantially inert with respect to the ceric methylsulfonate, the cerous methylsulfonate and the methanesulfonic acid.

By operating the process within the parameters just prescribed, it is possible to convert much of the biphenyl to 4-phenylquinol rather than to the over-oxidized byproduct, phenylbenzoquinone. The 4-phenylquinol can then be isomerized to phenylhydroquinone. The process provides a more economically attractive method to manufacture phenylhydroquinone, in that less ceric regeneration is required -- i.e. only ⅔rds as much ceric ion is reduced as compared to a process in which the biphenyl is oxidized to phenylbenzoquinone (sometimes hereinafter referred to as PBQ), and since there is less phenylbenzoquinone generated, less hydrogenation is necessary to convert phenylbenzoquinone to the desired product, phenylhydroquinone.

Preferred solvents for the biphenyl are nitriles, sulfones and dichloroalkanes. Mixtures of solvents are also useful.

Preferably the molar concentration of methanesulfonic acid in the aqueous mixture containing cerous methylsulfonate, ceric methylsulfonate and methanesulfonic acid is in the range of about 1 to about 5 moles per liter.

If desired the 4-phenylquinol can be separated from the reaction mixture by extraction, for example with 1,2-dichloroethane.

The 4-phenylquinol may be rearranged (isomerized) by use of an acid catalyst. Suitable catalysts include H₂SO₄, p-toluene sulfonic acid and acidic resins such as sulfonic acid cation exchange resin in the acid form and Nafion ® acid resins.

As a result of the oxidation of biphenyl, the ceric methylsulfonate is reduced to cerous methylsulfonate. The ceric methylsulfonate may be regenerated electrolytically, and the ceric methylsulfonate recycled for further oxidation of biphenyl. In other words, the process involves what the Kreh et al U.S. Pat. No. 4,670,108 calls "indirect electrochemical oxidation".

The process of the invention may be carried out in a batch reaction, or continuously.

DESCRIPTION OF THE DRAWING

The drawing shows a schematic flow sheet for the process of producing phenylhydroquinone from biphenyl.

DETAILED DESCRIPTION OF THE INVENTION

The solution of biphenyl in organic solvent is immiscible in the aqueous solution of ceric methylsulfonate, cerous methylsulfonate and methanesulfonic acid oxidizing agent. It is therefore highly desirable that the reaction be carried out under conditions of good mixing. After the reaction is complete, the reaction should be quenched by lowering the temperature, otherwise more of the 4-phenylquinol is converted to phenylbenzoquinone, and thus wastes the ceric ion which requires unnecessary regeneration with a corresponding increase in electric power consumption, and requires unnecessary hydrogenation.

The amount of ceric ion in the reaction mixture is always kept low so that 4-phenylquinol is not oxidized unnecessarily to phenylbenzoquinone.

At higher temperatures the rate of reaction is higher, but there is a tendency for the biphenyl to oxidize to phenylbenzoquinone thus reducing the oxidation efficiency.

The electrolytic regeneration of the ceric ion may be done in a flow-through cell at 540 amps/sq. ft. cell current density decreasing the cerous ion level to 0.16 moles per liter at less that 0.2 kilowatt hours/mole of ceric ion.

The FIGURE illustrates an overall process for the production of phenylhydroquinone from biphenyl; however the invention involves only the conditions in the oxidation step numbered 1 in the FIGURE.

In oxidizer 1, an aqueous mixture of ceric methylsulfonate, cerous methylsulfonate and methane sulfonic acid is combined with biphenyl dissolved in an organic solvent. Since the ingredients are immiscible, it is necessary to agitate the mixture.

From the oxidizer 1, the reaction mixture passes to decanter 2 where the phases are allowed to separate, and the less dense phase containing the ceric methylsulfonate, cerous methylsulfonate and methane sulfonic acid is removed from the upper portion of the decanter, and the phase containing the 4-phenylquinol as well as some phenylbenzoquinone is separated from the bottom portion of the decanter.

From the decanter 2, the phase containing the cerium is passed to extractor 3 where biphenyl is removed and the biphenyl is recycled to oxidizer 1.

The remaining portion of the cerium-containing phase is passed from extractor 3 to ceric regeneration cell 4, where the ceric ion is regenerated electrolytically to the desired level.

The phase containing the 4-phenylquinol that is separated in decanter 2, is passed to container 5 where it is subjected to isomerization using an acid catalyst to rearrange the 4-phenylquinol (4-PQ) to phenylhydroquinone (PHQ).

The isomerized product from container 5 is then passed to vacuum stripper 6 where remaining portions of solvent and water are removed.

The phenylhydroquinone containing some phenylbenzoquinone is then subjected to hydrogenation to convert the phenylbenzoquinone to phenylhydroquinone in hydrogenator 7.

The product from hydrogenator 7 is then subjected to distillation in column 8 to separate out the desired product phenylhydroquinone and remove the high boilers including any benzoic acid formed. Any biphenyl remaining in this phase is also removed and recycled to oxidizer 1.

In the following examples all parts and percentages are in parts by weight unless otherwise specified.

EXAMPLE 1

An oxidation reactor consisted of a heated 2-liter 4-inch diameter cylindrical glass vessel fitted with a four-bladed turbine agitator, baffles to enhance agitation and two dip tubes reaching to the bottom of the reactor to introduce feeds as well as an overflow tube that was adjustable in length so as to vary the working volume of the reactor. The product from the oxidation overflowed into a similar vessel which was immersed in a water bath to affect rapid cooling. This second vessel was also equipped with an agitator and a bottom drain to facilitate product removal as needed. A positive air pressure (25–30 psi) was maintained on the system. Material was discharged from the second vessel directly into a separatory funnel.

690 parts by volume of spent aqueous electrolyte containing 0.49 M/L cerous methanesulfonate[$Ce(CH_3SO_3)_3$], 0.01 M/L ceric methanesulfonate [$Ce(CH_3SO_3)_4$] and 3.36 M/L free methanesulfonic acid was charged to the oxidation reactor and heated to 60° C. while stirring. After reaching reaction temperature a mixture of 612 parts of biphenyl and 612 parts of acetonitrile was pumped into the reactor through one of the dip tubes while simultaneously 11,810 parts by volume of electrolytically regenerated aqueous electrolyte containing 0.19 M/L cerous methanesulfonate [$Ce(CH_3SO_3)_3$], 0.32 M/L ceric methanesulfonate [$Ce(CH_3SO_3)_4$] and 3.07 M/L free methanesulfonic acid was pumped into the reactor via the other dip tube. The pumping rate and the overflow tube was adjusted to achieve a 3.3 minute residence time in the reactor. Simultaneously with the above, 2581 parts of 1,2 dichloroethane was pumped into the receiver vessel cooled to 0° C. The resultant two phase reaction product was separated and the electrolyte (bottom layer) extracted with 3 portions of about 1000 parts of 1,2-dichloroethane followed by 2 portions of about 500 parts hexane. The extracted solutions were quantitatively analyzed. The analysis showed a 15.3% consumption of biphenyl and 80.3% yield of phenylbenzoquinone plus 4-phenylquinol. 29.5% of the combined product was as 4-phenylquinol. Analysis of the aqueous layer showed a 95.8% consumption of $Ce^{+4}$ at a $Ce^{+4}$/product ratio of 7.5.

EXAMPLES 2–14

The table below sets forth the results obtained when example 1 was repeated using the conditions specified in the table.

What is claimed:

TABLE

CONTINUOUS CERIC METHANESULFONATE OXIDATION OF BIPHENYL

| Example No. | Temperature (°C.) | Hold-Up Time (min) | $Ce^{4+}$ Consumed (%) | Biphenyl Consumption (%) | Product (PBQ + 4-PQ) Yield (%) | Product (PBQ + 4-PQ) Rate gM/L-Hr | $Ce^{4+}$/Product Ratio | Percent as 4-PQ | Remarks |
|---|---|---|---|---|---|---|---|---|---|
| 2 | 64.0 | 15.0 | 99.6 | 13.2 | 98.2 | 0.158 | 8.5 | 27.7 | 50 wt % Acetonitrile Feed |
| 3 | 80.0 | 5.3 | 94.5 | 10.7 | 100 | 0.318 | 8.6 | 12.4 | 50 wt % Acetonitrile Feed |
| 4 | 81.6 | 3.4 | 98.0 | 15.5 | 77.8 | 0.582 | 8.1 | 8.1 | 50 wt % Actenonitrile Feed |
| 5 | 81.0 | 3.4 | 97.0 | 17.9 | 67.8 | 0.570 | 8.4 | 5.4 | 50 wt % Acetonitrile Feed |
| 6 | 57.0 | 3.4 | 93.8 | 15.7 | 82.2 | 0.660 | 7.7 | 39.4 | 50 wt % Acetonitrile Feed |
| 7 | 46.0 | 3.6 | 30.5 | 10.6 | 57.5 | 0.260 | 8.2 | 48.3 | 60 wt % Dichloroethane Feed |
| 8 | 48.0 | 5.2 | 69.0 | 20.8 | 88.9 | 0.560 | 7.2 | 49.0 | 70 wt % Acetonitrile Feed |
| 9 | 56.0 | 5.9 | 67.0 | 16.1 | 66.2 | 0.540 | 7.0 | 44.6 | 33 wt % Dichloroethane Feed + 33 wt % Acetonitrile Feed |
| 10 | 57.0 | 4.8 | 97.4 | 21.1 | 49.0 | 0.510 | 7.2 | 44.0 | 33 wt % Sulfone + 33 wt % Acetonitrile Feed |
| 11 | 45.0 | 3.3 | 38.0 | 10.0 | 64.1 | 0.290 | 6.8 | 65.7 | 35 wt % Dichloroethane + 35 wt % Acetonitrile Feed |
| 12 | 55.0 | 4.1 | 61.0 | 12.0 | 73.1 | 0.310 | 7.9 | 53.3 | 35 wt % Dichloroethane + 35 wt % Acetonitrile Feed |
| 13 | 49.0 | 12.1 | 76.7 | 12.0 | 65.0 | 0.130 | 7.4 | 30.8 | 35 wt % Dichloroethane + 35 wt % Acetonitrile Feed |

1. A process for the preparation of 4-phenylquinol which comprises oxidizing at a temperature in the range of 20 to 90 degrees C., biphenyl dissolved in an organic solvent with an aqueous mixture of cerous methanesulfonate, ceric methanesulfonate and methanesulfonic acid, in which the mole ratio of cerous methanesulfonate to ceric methanesulfonate is in the range of about 0.2 to 50 mole percent, and the solvent is substantially inert with respect to the ceric methanesulfonate, the cerous methanesulfonate and the methanesulfonic acid.

2. The process of claim 1 in which the biphenyl is dissolved in an organic solvent selected from the class consisting of nitriles, sulfones and dichloroalkanes.

3. The process of claim 1 in which the aqueous mixture of cerous methanesulfonate, ceric methanesulfonate and methanesulfonic acid contains a molar concentration of methanesulfonic acid in the range of about 1 to about 5 moles per liter.

4. The process of claim 1 in which the 4-phenylquinol is separated from the reaction mixture by extraction with 1,2-dicholorethane.

5. The process of claim 1 in which the 4-phenylquinol is rearranged in the presence of an acid catalyst to form phenyl hydroquinone.

6. A process for the preparation of phenyl hydroquinone which comprises oxidizing biphenyl with a mixture of cerous methanesulfonate, ceric methanesulfonate and methanesulfonic acid to form 4-phenylquinol, and rearranging the 4-phenylquinol to phenyl hydroquinone in the presence of an acid catalyst.

* * * * *